United States Patent
Griswold et al.

(10) Patent No.: US 9,066,673 B2
(45) Date of Patent: Jun. 30, 2015

(54) WIRELESS/INTERVENTION-INDEPENDENT SCAN PLANE CONTROL FOR AN MRI TO TRACK A CATHETER IN A BODY

(76) Inventors: Mark A. Griswold, Shaker Heights, OH (US); Matthew Riffe, Cleveland Heights, OH (US); Stephen Yutzy, University Heights, OH (US); Vikas Gulani, Shaker Heights, OH (US); Dean Nakamoto, Beachwood, OH (US); Daniel Hsu, Shaker Heights, OH (US)

( * ) Notice: Subject to any disclaimer, the term of this patent is extended or adjusted under 35 U.S.C. 154(b) by 804 days.

(21) Appl. No.: 12/873,395

(22) Filed: Sep. 1, 2010

(65) Prior Publication Data

US 2012/0053448 A1    Mar. 1, 2012

(51) Int. Cl.
| | | |
|---|---|---|
| A61B 5/055 | (2006.01) | |
| A61B 5/06 | (2006.01) | |
| A61B 19/00 | (2006.01) | |
| A61B 5/00 | (2006.01) | |

(52) U.S. Cl.
CPC ......... *A61B 5/055* (2013.01); *A61B 2019/2292* (2013.01); *A61B 2019/5251* (2013.01); *A61B 2019/5236* (2013.01); *A61B 5/721* (2013.01); *A61B 2019/5289* (2013.01); *A61B 5/062* (2013.01)

(58) Field of Classification Search
CPC ........... A61B 5/721; A61B 2019/5236; A61B 2019/2292; A61B 2019/5251; A61B 2019/5289
See application file for complete search history.

(56) References Cited

U.S. PATENT DOCUMENTS

| | | | |
|---|---|---|---|
| 6,275,721 B1 * | 8/2001 | Darrow et al. | 600/410 |
| 6,516,213 B1 * | 2/2003 | Nevo | 600/424 |
| 7,596,402 B2 | 9/2009 | Duerk et al. | |
| 2005/0054914 A1 * | 3/2005 | Duerk et al. | 600/423 |
| 2006/0244452 A1 * | 11/2006 | Den Boef | 324/322 |
| 2007/0015960 A1 * | 1/2007 | Gornert et al. | 600/102 |
| 2010/0156412 A1 * | 6/2010 | Biber et al. | 324/307 |
| 2011/0012594 A1 * | 1/2011 | Kimura et al. | 324/309 |

OTHER PUBLICATIONS

Riffe et al. Real-time Scan Plane Selection with a Novel Hand-held Device for Needle Guidance, Proc. Intl. Soc. Mag. Reson. Med. 19 (2011).*
Riffe et al, Using On-board Microprocessors to Control a Wireless MR Receiver Array, Proc. Intl. Soc. Mag. Reson. Med. 17 (2009).*
Krieger, et al., Design of a Novel MRI Compatible Manipulator for Image Guided Prostate Interventions; IEEE Transactions on Biomedical Engineering, vol. 52, No. 2, Feb. 2005; pp. 306-313.

* cited by examiner

*Primary Examiner* — Unsu Jung
*Assistant Examiner* — Serkan Akar

(57) ABSTRACT

Example systems, apparatus, circuits, and so on described herein concern intervention-independent scan plane control for an MRI system. A tracking device capable of being manipulated independently of an interventional device in use to treat a patient transmits position signals describing an orientation of the tracking device to an MRI system. The MRI system determines a desired scan plan that will correspond to the orientation of the tracking device and performs a diagnostic scan on the desired scan plan.

3 Claims, 8 Drawing Sheets

WIRELESS/INTERVENTION-INDEPENDENT SCAN PLANE CONTROL FOR AN MRI TO TRACK A CATHETER IN A BODY

BACKGROUND

Magnetic Resonance Imaging (MRI) systems are often employed to provide guidance to interventionalists who are performing interventional procedures that diagnose or treat tissue within a patient. In interventional procedures an interventional device may be guided by an interventionalist to a target tissue within a patient. Interventional devices may include, for example, needles, catheters, ablation devices, imaging devices, therapeutic devices, diagnostic devices, and so on. In an image guided interventional device insertion, the location of the device relative to the surrounding anatomy and target are determined using the MRI system.

To assist in MRI image guided interventional procedures, many techniques have been developed that track the location of an interventional (intracorporeal) device and update scan planes used by the MRI system so that the scan planes track the device. However, in some circumstances these techniques, which fix the scan plane relative to the interventional device, produce unsatisfactory results. For example, flexing of a catheter or needle on the device may cause misregistration of the scan plane and the tissue in treatment. In other instances, the interventionalist performing the procedure may wish to view an image that does not correspond to a scan plane in the fixed relationship to the interventional device being used on the patient. When a different scan plan is desired, a time consuming manual adjustment of the scan plane must be performed.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

The apparatus, methods, and systems described herein allow an interventionalist to specify a desired scan plane in a manner that is intervention-independent. In this context, intervention-independent scan plane control means that the scan plane is not automatically determined in relation to any interventional device, but rather is specified by the interventionalist substantially in real-time. The interventionalist may decide on a scan plane based, for example, on tactile feedback received from a needle or catheter that the interventionalist is manipulating within the patient.

Figure 1:
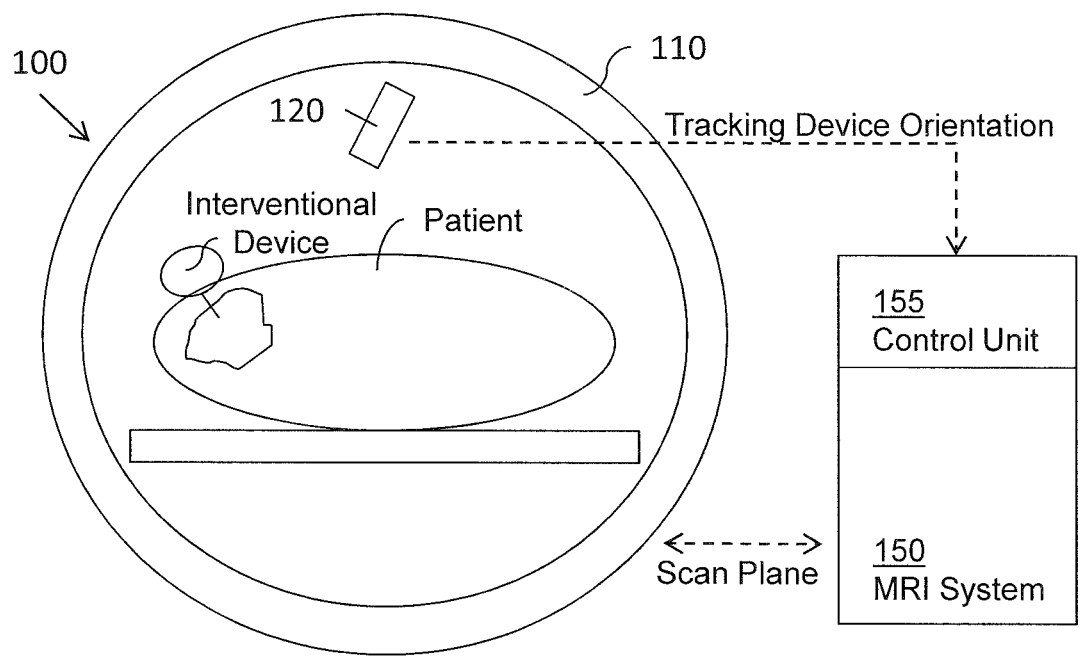
FIG. 1 schematically illustrates an example embodiment of an MRI apparatus that includes an intervention-independent device for scan plane control.

Thus intervention-independent scan control can be performed whether or not an interventional device is in use on the patient because the scan plane is not determined relative to any interventional device. To realize intervention-independent scan plane control, a tracking device for specifying a scan plane is provided. A method of controlling an MRI imaging system to acquire an image according to an intervention-independent scan plane and an MRI system for performing imaging based on an intervention-independent scan plane are also provided FIG. 1 is a schematic illustration of an example embodiment of an MRI system 100 that employs intervention-independent scan plane control. A patient and an interventional device being used to access tissue within the patient are shown located within a bore of an MRI magnet 110. A tracking device 120 is being manipulated by an interventionalist (not shown) to specify a desired scan plane. Signals corresponding to an orientation of the tracking device are transmitted, in some instances wirelessly, from the tracking device 120 to an MRI control unit 155 that is part of an MRI imaging system 150. The control unit 155 converts the information about the orientation of the tracking device into a desired scan plane. The MRI imaging system 150 is controlled to produce an image of the patient along the desired scan plan.

The images produced by the MRI imaging system 150 may be used by the interventionalist to guide an interventional device within the patient. For example, the interventionalist may be performing an MRI guided biopsy. As the interventionalist advances the needle towards a target region (e.g., lesion, tumor, mass, volume) with one hand, the interventionalist may control the MR scan plane by manipulating the device 120 with the other hand.

Figure 2:
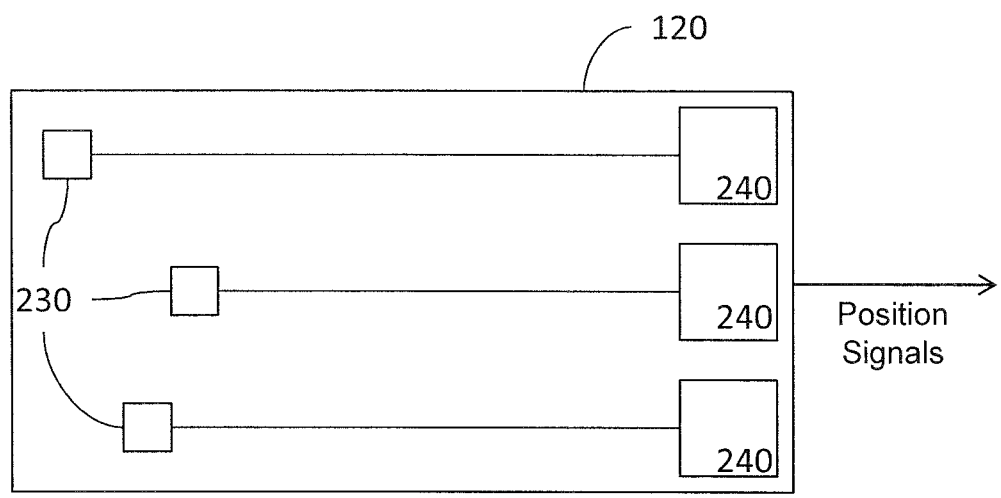
FIG. 2 schematically illustrates an example embodiment of a tracking device for intervention-independent scan plane control.

FIG. 2 illustrates an example embodiment of the tracking device 120. The tracking device 120 includes three markers 230 that are configured to produce position signals corresponding to positions of the markers 230. The position signals produced by the markers 230 are sufficient to describe a desired scan plane for an MRI imaging system. The position signals may be typical MR image signals that can be used by the MRI system to determine spatial coordinates of each marker. While three markers 230 are shown in FIG. 2, other numbers of markers that can sufficiently describe a desired scan plane may be used. The markers 230 are positioned with non-uniform spacing between them. This non-uniform spacing enables the individual markers 230 to be distinguished based on their relative positions.

Figure 3:
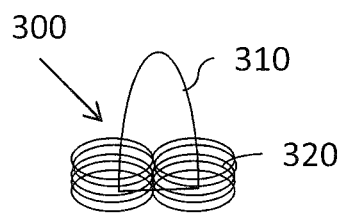
FIG. 3 schematically illustrates an example embodiment of an active tracking marker that can be used in a tracking device for intervention-independent scan plane control.

FIG. 3 is a schematic illustration of a marker embodied as an active tracking marker 300 that is responsive to excitation from the MRI magnetic field to produce the position signals. The active tracking marker 300 comprises a fiducial marker 310 coupled to a microcoil 320. The fiducial marker 310 may be a vitamin E capsule or other fluid filled vessel that will properly respond to the magnetic field. The microcoil 320 may be embodied as a multi-turn butterfly coil, or gradiometer, or other configuration that provides a signal in all positions relative to the magnetic field. Traditional coils will not produce a signal when aligned perfectly with the field.

Referring back to FIG. 2, the tracking device 120 also includes three transmitters 240 configured to transmit the position signals to an MRI system. While one transmitter per marker is shown in FIG. 2, different numbers of transmitters could be used. The tracking device 120 may also include additional electronic and mechanical components that are not shown in FIG. 2, such as signal conditioning components like on-board amplifiers and a power source. In one particular embodiment, the tracking device 120 is wireless.

In one example wireless tracking device, the transmitters are configured to transmit the position signals wirelessly to the MRI imaging system using amplitude modulation. One example MRI imaging system that has been developed to wirelessly receive image signals from multiple channels simultaneously using amplitude modulation encoding is described in "Using On-board Microprocessors to Control a Wireless MR Receiver Array.") Matthew J. Riffe, Jeremiah A. Heilman, Natalia Gudino, Mark A. Griswold, Using On-Board Microprocessors to Control a Wireless MR Receiver Array, Proceedings 17th Scientific Meeting, International Society for Magnetic Resonance in Medicine 2009: 2936.

Unlike prior art devices, the tracking device 120 transmits position signals that describe a desired scan plane without signal or mechanical interaction with an interventional device that may be in use to treat a patient. The desired scan plan described by the position signals is used by the MRI imaging system 150 (FIG. 1) to perform a subsequent scan of the patient independent of a position of an interventional device in use to treat a patient. To facilitate ease of manipulation the markers 230 and transmitters 240 may be located in a housing configured to be held in the hand. While no direct interaction between the interventional device and the tracking device 120 exists, an indirect interaction may be mediated by the interventionalist. The interventional device may be, for example, a catheter, a needle, an ablation device, an imaging device, a therapeutic device, a diagnostic device, and so on.

Figure 4:
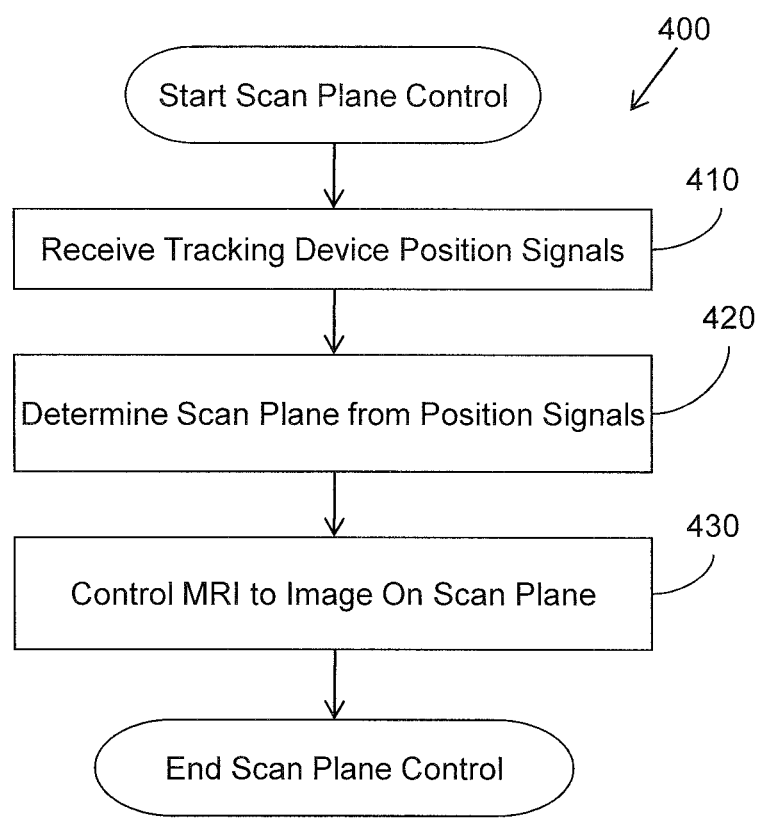
FIG. 4 is a flow diagram that illustrates an example embodiment of a method for performing intervention-independent scan plane control.

FIG. 4 is a flow diagram outlining an example of a method 400 for performing intervention-independent scan plane control. The method 400 may be performed by an MRI control unit 155 (FIG. 1). At 410, the method 400 includes receiving, from a tracking device being manipulated independently of an interventional device in use to treat a patient, position signals that describe an orientation of the tracking device. The receiving may be performed by wirelessly receiving amplitude modulated signals describing an orientation of the tracking device. At 420, a scan plan is determined that will correspond to the orientation of the tracking device. At 430, the method includes controlling an MRI imaging system to perform a scan on the determined scan plan. For example, as a surgeon is performing a needle biopsy on a patient, the tracking device can be manipulated by the surgeon to cause the MRI system to perform a scan plane aligned with the orientation of the tracking device.

Figure 5:
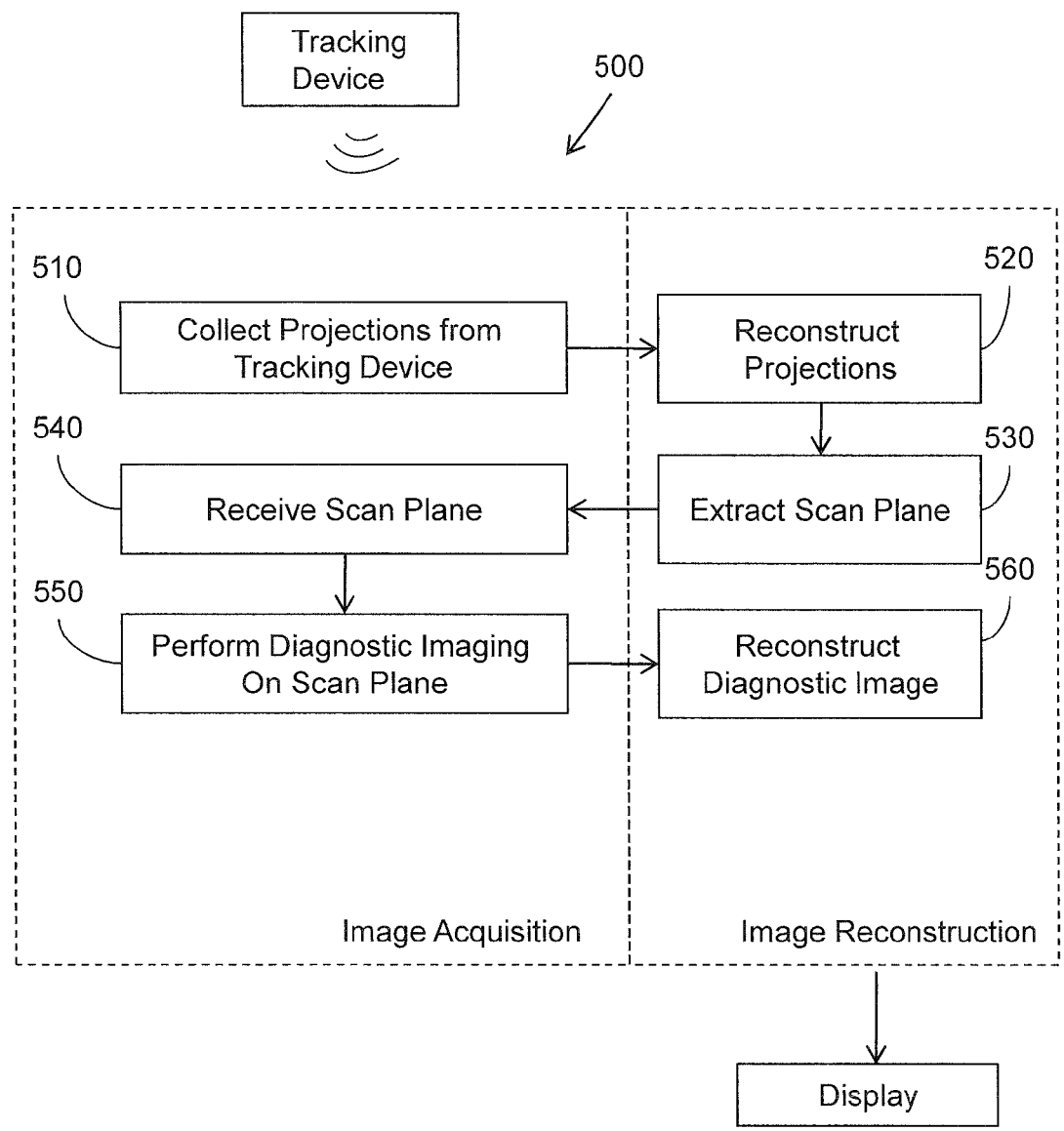
FIG. 5 is a flow diagram that illustrates another example embodiment of a method for performing intervention-independent scan plane control.

FIG. 5 is a flow diagram outlining an example of a method 500 for performing intervention-independent control of a scan plane. For clarity, image acquisition and image reconstruction components in an MRI system are shown as dashed line regions and actions performed by the component are located within the region. At 510 image data including tracking projections in three orthogonal axes for the markers is collected by the image acquisition components from a tracking device. The image data may be collected using, for example, a FLASH (fast low angle shot MRI) sequence that has been modified to collect the tracking projections. At 520 the tracking projections are reconstructed by performing Fourier transform operations on the tracking projections in the axes and determining a position with respect to the axes for the markers using magnitude reconstruction on the output of the Fourier transform operations. At 530 the method includes extracting a scan plane that intersects the determined position of the markers.

At 540, image acquisition receives the scan plane and at 550 performs diagnostic imaging on the scan plane. At 560 the image data from the scanner is reconstructed into a diagnostic image for display. As can be seen from FIG. 5, the reconstructed image is independent of an interventional device and is determined by the position data received from the tracking device.

Figure 6:
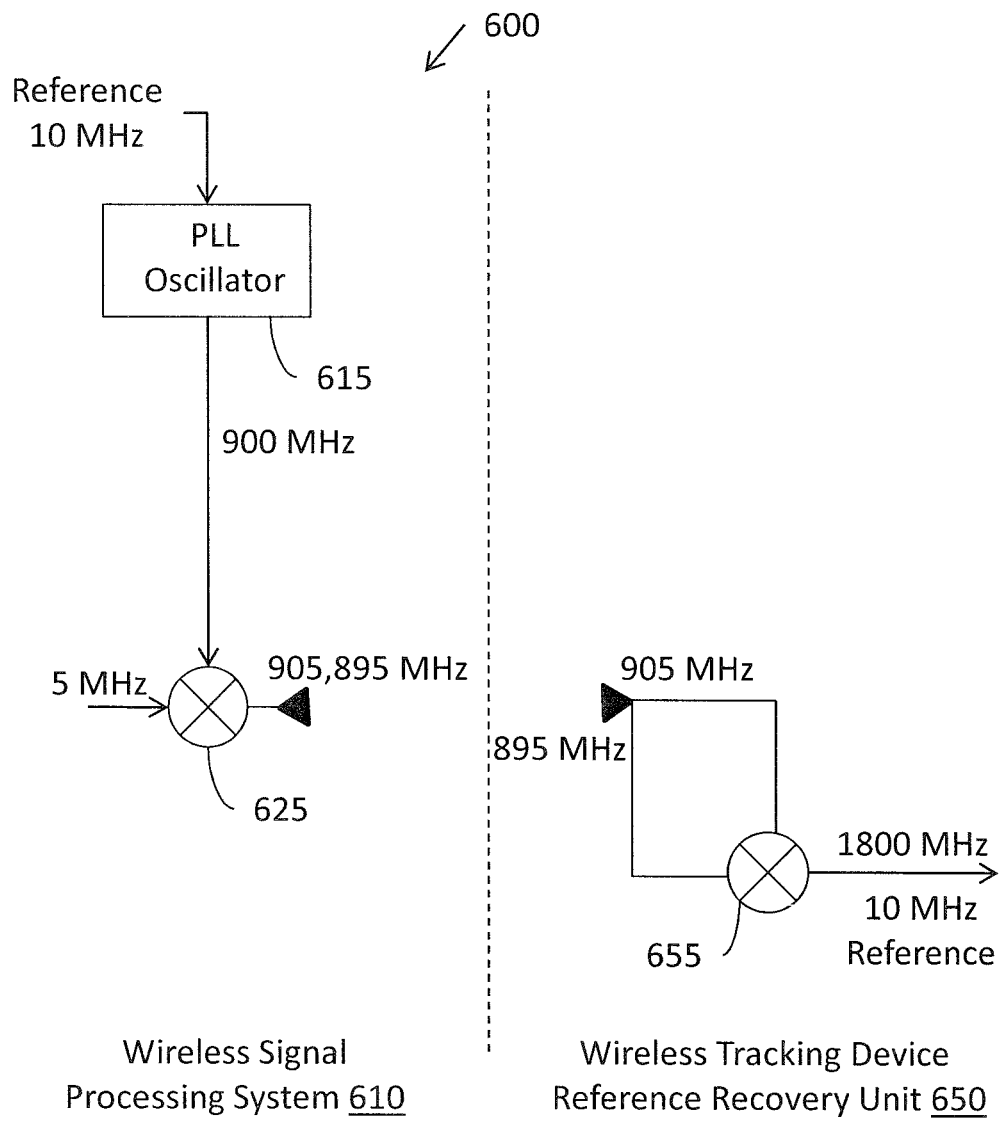
FIG. 6 schematically illustrates an example embodiment of a reference signal recovery system associated with intervention-independent scan plane control.

FIG. 6 is a schematic illustration of a system 600 for wirelessly transmitting a reference signal for synchronizing a tracking device to a wireless signal processing unit 610 associated with an MRI system that will be receiving position data from the tracking device. A low frequency 10 MHz signal is the reference signal in the illustrated example. The low frequency signal may be provided by the MR scanner to synchronize electronics in the MR scanner. Generally, the handheld device may be controlled, at least in part, by the synchronizing signal from the MR scanner. However, in the embodiments illustrated in FIGS. 7 and 8, a different approach is illustrated. A phase locked loop (PLL) oscillator circuit 615 generates a high frequency (900 MHz) carrier frequency. The carrier frequency signal is mixed with a 5 MHz signal to produce sideband component frequencies of 905 and 895 MHz. The sideband component frequencies are transmitted to a wireless tracking device reference recovery unit 650 on the tracking device. The wireless tracking device reference recovery unit 650 receives the high frequency upper and lower sideband components and mixes them to recover the low frequency reference signal of 10 MHz.

Figure 7:
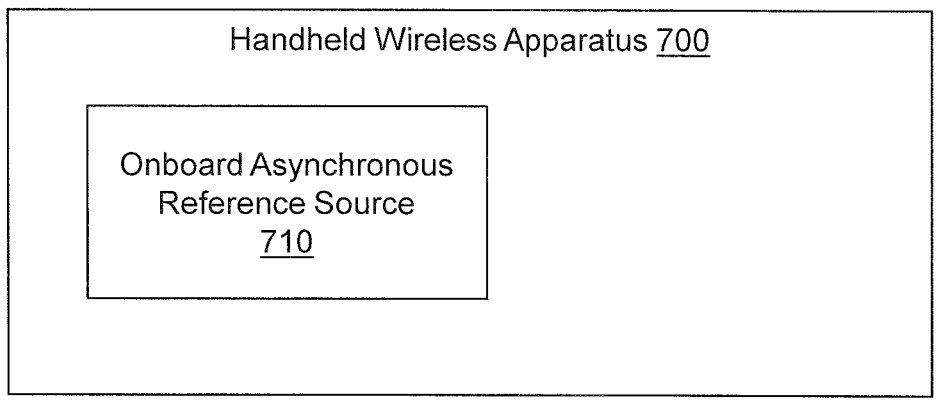
FIG. 7 illustrates a handheld wireless device for use in an MRI system, where the handheld wireless device generates an onboard asynchronous reference signal.

FIG. 7 illustrates a handheld wireless apparatus 700. Apparatus 700 may be used in conjunction with an MRI system. Handheld wireless apparatus 700 is configured to generate its own onboard asynchronous reference signal using onboard asynchronous reference source 710. In one example, the asynchronous reference signal is asynchronous to the synchronization signal provided by an MR scanner as described above. In one example, the onboard asynchronous reference source 710 may be a ceramic oscillator. Recall that apparatus 700 may be employed in an MRI bore and thus be subjected to intense magnetic fields. In one example, the ceramic oscillator may be a 5 MHz ceramic oscillator. In another, the ceramic oscillator may be a 10 MHz ceramic oscillator. One skilled in the art will appreciate that other frequencies (e.g., 20 MHz) may be employed. In one example, the ceramic oscillator will be configured to produce a signal whose frequency shift error is less than 20 ppm. One skilled in the art will appreciate that signals with other qualities (e.g., frequency shift error up to 100 ppm) may be generated. In one embodiment, the onboard asynchronous reference source 710 is configured to produce a carrier frequency to facilitate transmitting the position signals to the MR scanner.

Figure 8:
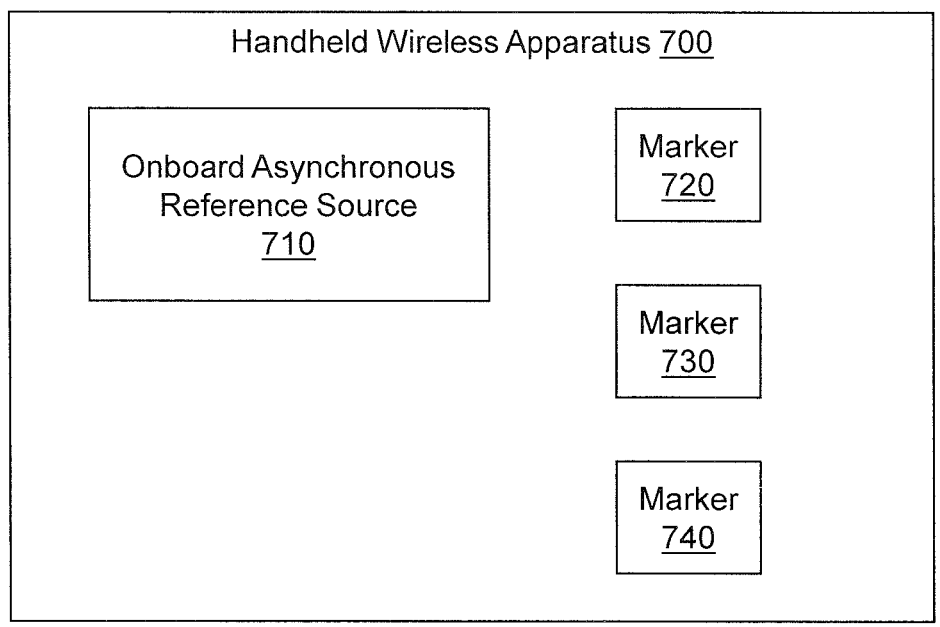
FIG. 8 illustrates a handheld wireless device for use in an MRI system, where the handheld wireless device generates an onboard asynchronous reference signal.

FIG. 8 illustrates another embodiment of handheld wireless apparatus 700. This embodiment of apparatus 700 includes three markers 720, 730, and 740 that correspond to the markers described above that produce position signals sufficient to describe a desired MR scan plane.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. An intervention-independent device for scan plane control, comprising:
    a plurality of markers configured to produce position signals corresponding to positions of the markers, where the position signals describe an orientation of the device, where the position signals are magnetic resonance signals from which the spatial coordinates of a marker or the orientation of a marker can be determined, where the position signals are sufficient to describe a desired magnetic resonance (MR) scan plane, where the markers comprise active markers that are responsive to excitation from the MRI magnetic field to produce the position signals, where the markers comprise coils;
    one or more transmitters configured to transmit the position signals to a magnetic resonance imaging (MRI) system using one or more of, amplitude modulation, and frequency modulation;
    a wireless reference recovery circuit configured to receive a mixed signal comprising high frequency upper and lower sideband components of a low frequency reference signal and to mix the received high frequency components upper and lower sideband components to recover the low frequency reference signal, where the low frequency reference signal is used to synchronize the device with the MRI system for wireless communication, the high frequency upper sideband being a greater frequency than the high frequency lower sideband, and the high frequency upper sideband and high frequency lower sideband having a greater frequency than the low frequency reference signal;
    an onboard asynchronous reference source configured to produce a second reference signal asynchronous to the low frequency reference signal associated with the MRI system, and to produce a carrier frequency to facilitate transmitting the position signals, and
    a housing configured to be held by an interventionalist, where the housing houses the markers and transmitters;
    where the markers and transmitters operate without signal or mechanical interaction with an interventional device in use to treat a patient; and
    where the MRI system is controlled to perform a subsequent scan of the patient along the desired scan plane independent of a position of an interventional device in use to treat the patient.

2. The device of claim 1, the onboard asynchronous reference source being a ceramic oscillator having an oscillation frequency in the range of 5 MHz to 10 MHz and configured to produce the second reference signal with a frequency shift error in the range of 1 ppm to 100 ppm.

3. A method for automatically controlling an MRI system, comprising:
    wirelessly receiving, in the MRI system, from a device being manipulated independently of an interventional device in use to treat a patient, position signals describing an orientation of the device, where the receiving is performed by wirelessly receiving one or more of, amplitude modulated signals describing an orientation of the device, and frequency modulated signals describing an orientation of the device;
    wirelessly receiving a reference signal for use in synchronizing the position signals from the device with the MRI system, where the receiving of a reference signal comprises:
        receiving a mixed signal comprising high frequency upper and lower side band frequencies for a low frequency reference signal; and
        reconstructing the low frequency reference signal by mixing the upper and lower side band frequencies of the mixed signal,
        where the upper side band frequency and the lower side band frequency are higher than the frequency of a detected MRI signal;
    determining a scan plane that will correspond to the orientation of the device by:
        collecting in the MRI system image data including projections in three orthogonal axes for each marker;
        performing Fourier transform operations on the projection in each axis;
        determining a position with respect to each axis for the markers using magnitude reconstruction on the output of the Fourier transform operations; and
        constructing a scan plane that intersects the determined positions of the markers; and
    automatically controlling the MRI system to perform a scan on the determined scan plane.

* * * * *

UNITED STATES PATENT AND TRADEMARK OFFICE
CERTIFICATE OF CORRECTION

| | | |
|---|---|---|
| PATENT NO. | : 9,066,673 B2 | Page 1 of 1 |
| APPLICATION NO. | : 12/873395 | |
| DATED | : June 30, 2015 | |
| INVENTOR(S) | : Griswold et al. | |

It is certified that error appears in the above-identified patent and that said Letters Patent is hereby corrected as shown below:

ON THE TITLE PAGE

In the Abstract item 57:

In line 7, delete "plan" and insert --plane--.

In line 9, delete "plan" and insert --plane--.

IN THE SPECIFICATION

In column 1, line 31, delete "plan" and insert --plane--.

In column 2, line 43, delete "plan" and insert --plane--.

In column 3, line 35, delete "plan" and insert --plane--.

In column 3, line 56, delete "plan" and insert --plane--.

In column 3, line 59, delete "plan" and insert --plane--.

Signed and Sealed this
Seventeenth Day of November, 2015

Michelle K. Lee
*Director of the United States Patent and Trademark Office*